US012734267B2

(12) United States Patent
Jeong

(10) Patent No.: US 12,734,267 B2
(45) Date of Patent: Sep. 15, 2026

(54) METHOD FOR MANUFACTURING HEMOSTATIC MEDICAL MATERIAL

(71) Applicant: In Sun Jeong, Gwangju (KR)

(72) Inventor: In Sun Jeong, Gwangju (KR)

( * ) Notice: Subject to any disclaimer, the term of this patent is extended or adjusted under 35 U.S.C. 154(b) by 710 days.

(21) Appl. No.: 18/043,305

(22) PCT Filed: Aug. 20, 2021

(86) PCT No.: PCT/KR2021/011107
§ 371 (c)(1),
(2) Date: Dec. 13, 2023

(87) PCT Pub. No.: WO2022/050609
PCT Pub. Date: Mar. 10, 2022

(65) Prior Publication Data

US 2024/0115757 A1 Apr. 11, 2024

(51) Int. Cl.

| | |
|---|---|
| ***A61L 15/28*** | (2006.01) |
| ***A61F 13/00*** | (2024.01) |
| ***A61F 13/01*** | (2024.01) |
| ***A61L 15/44*** | (2006.01) |
| ***A61L 17/10*** | (2006.01) |
| ***A61L 17/14*** | (2006.01) |

(52) U.S. Cl.
CPC ........ *A61L 15/28* (2013.01); *A61F 13/00991* (2013.01); *A61F 13/01012* (2024.01); *A61L 15/44* (2013.01); *A61L 17/10* (2013.01); *A61L 17/14* (2013.01); *A61L 2300/604* (2013.01); *A61L 2400/04* (2013.01)

(58) Field of Classification Search
None
See application file for complete search history.

(56) References Cited

U.S. PATENT DOCUMENTS

| | | | | |
|---|---|---|---|---|
| 2002/0156498 A1* | 10/2002 | Jo | ........................ | A61K 31/717 606/213 |
| 2019/0194359 A1 | 6/2019 | Eliyahu-Gross et al. | | |

FOREIGN PATENT DOCUMENTS

| | | |
|---|---|---|
| JP | 2752782 B2 | 5/1998 |
| JP | 2001-231847 A | 8/2001 |
| JP | 3576063 B2 | 10/2004 |
| KR | 2004-0086072 A | 10/2004 |
| KR | 10-1318421 B1 | 10/2013 |
| KR | 10-1321724 B1 | 10/2013 |
| KR | 2014-0099301 A | 8/2014 |
| KR | 2016-0034256 A | 3/2016 |
| KR | 10-1699924 B1 | 1/2017 |

OTHER PUBLICATIONS

International Search Report issued in PCT/KR2021/011107; mailed Dec. 6, 2021.

Sim, Eun Jung et al.; "Fabrication of Bioabsorbable Poly(vinyl pyrrolidone) Nanofibrous Sheets Containing Blood Coagulants for Hemostatic Application"; Polymer Science and Technology(Korea); 2019; vol. 43, No. 4; pp. 629-639; https://doi.org/10.7317/pk.2019.43.4.629; with partial English translation.

* cited by examiner

*Primary Examiner* — Isis A Ghali
(74) *Attorney, Agent, or Firm* — Studebaker Brackett PLLC

(57) ABSTRACT

Proposed are a method of manufacturing a hemostatic medical material that has excellent biosafety and can be applied to various situations by controlling the decomposition rate as necessary, and a medical material manufactured thereby. The method includes pretreating a natural cellulose substrate by adjusting the pH of the substrate, causing the hemostatic agent to be adsorbed on the pretreated substrate, drying the substrate with the hemostatic agent adsorbed thereon, primarily modifying the dried substrate using monochloroacetic acid (MCA), secondarily modifying the primarily modified substrate using an organic acid aqueous solution, washing the secondarily modified substrate, and post treating the substrate by adjusting the pH of the washed substrate.

1 Claim, No Drawings

METHOD FOR MANUFACTURING HEMOSTATIC MEDICAL MATERIAL

CROSS-REFERENCE TO RELATED APPLICATIONS

This application is a U.S. National Phase Entry of International Application No. PCT/KR2021/011107 filed on Aug. 20, 2021, which claims the benefit of priority to Korean Patent Application No. 10-2020-0111050 filed on Sep. 1, 2020, the entire content of which is incorporated herein by reference.

TECHNICAL FIELD

The present disclosure relates to a method for manufacturing a medical material capable of controlling hemostasis and decomposition rate for blood or human body water and to a medical material manufactured thereby. More particularly, the present disclosure relates to a method of manufacturing a medical material and medical material manufactured thereby, in which a hemostatic agent is adsorbed on a natural cellulose substrate in the form of a fiber or a nonwoven fabric, and the decomposition rate is controlled after being modified with a monochloroacetic acid (MCA) and an organic acid.

BACKGROUND ART

Skin is a body organ that protects the human body from external stimuli, prevents moisture loss, and performs important life protection functions such as regulating body temperature and preventing bacterial invasion. If the skin loses function due to various trauma, the skin can cause various side effects such as moisture loss and bacterial infection from the outside, making the affected area difficult to treat, or secondary dysfunction, which in severe cases affects life extension. Therefore, in order to rapidly treat wounds and minimize various side effects, it is essential to treat wounds using appropriate dressings.

Initially, a bandage with excellent moisture absorption was used as a dressing used for skin wounds, and nonwoven fabrics made of natural biodegradable cellulose such as cotton, hemp, bamboo, and corn have been used for this bandage.

However, cotton dressing manufactured through this method does not absorb all the wound secretions generated from skin wounds. As the unabsorbed wound secretion dries, the cotton dressing is attached to the wound surface, making it difficult to change to a new one, and there are problems such as damaging new skin tissues and causing pain.

On the other hand, general transparent film dressing materials only have characteristics to block infection with the outside but do not have absorption power, so their use is limited if there is exudate or bleeding. Recently, since wound treatment is more efficient in a wet environment than in a dry environment, studies on wet wound cladding have been mainly conducted.

On the other hand, in order to treat trauma, such dressing materials are used to prevent exposure to the affected area or to sew the affected area using threads. If these dressing materials or threads contain hemostatic components, immediate hemostatic action occurs in the affected area, which may rather interfere with surgery.

Accordingly, it is necessary to develop a medical material that can exert a hemostatic effect by applying a hemostatic agent to medical materials such as dressing materials and medical threads and, at the same time, adjust the speed of hemostasis initiation so that the medical material can be used in various situations.

DISCLOSURE

Technical Problem

The present disclosure provides a method for manufacturing a medical material capable of controlling the hemostatic and decomposition rate of blood or human body water and a medical material manufactured thereby, in which a hemostatic component is adsorbed on a natural cellulose substrate in the form of fiber or nonwoven fabric, and the decomposition rate is controlled after being modified with monochloroacetic acid (MCA) and organic acid.

Technical Solution

A method for manufacturing a medical material according to an embodiment of the present disclosure for achieving the above objective, the method includes: pretreating a natural cellulose substrate by adjusting the pH of a natural cellulose substrate; causing a hemostatic agent to be adsorbed on the pretreated substrate; drying the substrate on which the hemostatic agent is adsorbed; a primarily modifying the dried substrate using monochloroacetic acid (MCA); a secondarily modifying the primarily modified substrate using an organic acid aqueous solution; and a post-treating to adjust the pH of the secondarily modified substrate.

It is preferable that washing the secondarily modified substrate is performed between the secondary modifying and the post-treating.

In addition, in adsorbing the hemostatic agent, it is preferable that the pretreated substrate is immersed in an aqueous solution containing the hemostatic agent and the fixing agent.

Between adsorbing the hemostatic agent and drying, fixing in which the substrate adsorbed with the hemostatic agent is immersed in an aqueous solution of hyaluronic acid may be performed.

The organic acid aqueous solution used in the secondary modifying step preferably contains at least one selected from the group consisting of citric acid and ascorbic acid.

In the organic acid aqueous solution, it is more preferable that citric acid and ascorbic acid are mixed in a weight ratio of 10:2 to 5.

Before the post-treating is performed, controlling the decomposition rate by immersing the substrate in the gelling agent diluent after washing may be performed.

The hemostatic agent may include at least one selected from the group consisting of thrombin, thromboplastin, fibrinogen, casein-kinase II, tissue factors, aluminum hydroxide, aprotinin, and calcium chloride dihydrate.

The primary modifying may be performed in a multi-step manner in which the dried substrate is immersed in a solvent, a base is added, and then MCA is introduced.

As another embodiment of the present disclosure, a medical material produced by this method can be mentioned.

Advantageous Effects

The method for manufacturing a medical material capable of controlling hemostasis and decomposition rate for blood or human body water according to the present disclosure and the medical material manufactured according to the method have an excellent hemostatic effect, and the decomposition rate of the medical material can be controlled as needed. Therefore, wound treatment efficiency can be increased by controlling the decomposition rate according to the purpose of using the medical material.

BEST MODE

Hereinafter, before being described in detail through a preferred embodiment of the present disclosure, it will be noted that terms or words used in the present specification and claims should not be limited to general or dictionary meanings but should be interpreted as meanings and concepts conforming to the technical idea of the present disclosure.

Throughout this specification, when a part "includes" a certain component, it means that other components may be further included rather than excluding other components unless otherwise stated.

Throughout this specification, the "%" used to indicate the concentration of a particular substance means (weight/weight) % for solid/solid, (weight/volume) % for solid/liquid, and (volume/volume) % for liquid/liquid, unless otherwise stated.

Hereinafter, an embodiment of the present disclosure will be described. However, the scope of the present disclosure is not limited to the following preferred embodiments, and those skilled in the art can implement various modified forms of the contents described herein within the scope of the present disclosure.

The present disclosure relates to a medical material for hemostasis. More specifically, the present disclosure relates to a method for manufacturing a hemostatic and decomposition rate controllable medical material that can be applied to various situations, such as urgently requiring hemostasis, requiring sustained release hemostasis, minimizing early hemostasis effects, and maximizing late hemostasis effects, such as during surgery by controlling the dissolution rate of the hemostatic agent by adjusting the decomposition rate of the medical material for hemostasis as necessary while exhibiting the hemostatic effect by the hemostatic agent and having excellent biosafety, and a medical material manufactured thereby.

First, the method for manufacturing a medical material capable of controlling hemostasis and decomposition rate according to an embodiment of the present disclosure, the method includes: pretreating a natural cellulose substrate by adjusting the pH of the natural cellulose substrate; causing a hemostatic agent to be adsorbed on the pretreated substrate; drying the substrate on which the hemostatic agent is adsorbed; a primarily modifying the dried substrate using monochloroacetic acid (MCA); a secondarily modifying the primarily modified substrate using an organic acid aqueous solution; washing the secondarily modified substrate; and a post-treating the washed substrate by adjusting the pH of the washed substrate.

The natural cellulose substrate used as the substrate for the medical material of the present disclosure may be a fiber (thread) or non-woven fabric made of natural biodegradable cellulose such as cotton, hemp, bamboo, and corn. These natural cellulose substrates are generally supplied through primary processing such as scouring, degreasing, and bleaching using hydrogen peroxide. Since the natural cellulose substrate subjected to the primary processing generally has a pH in the range of 5.5 to 7 and a scouring state or degreasing state is not uniform, pretreating is performed to uniformize and stabilize the state of the natural cellulose substrate in the present disclosure.

The pretreating is performed to adjust the pH to a level of scouring higher than a predetermined level, uniform degreasing, and maximally increasing the adsorption efficiency of hemostatic components.

The pretreating may be performed by immersing and reacting the substrate in a basic aqueous solution. Specifically, the pretreating may be performed by immersing a substrate in purified water at 90° C. to 110° C., adding 0.1 to 1 part by weight of a base based on 100 parts by weight of the substrate, and reacting the substrate for 40 to 90 minutes. At this time, the weight ratio of the purified water and the substrate may be 6 to 8:1.

The base is not particularly limited, such as NaOH, KOH, $Ca(OH)_2$, $Ba(OH)_2$, and NaOH may be preferably used.

Through this step, it is preferable that the pH of the substrate is adjusted to 8 to 8.8. If the pH is less than 8, the adsorption efficiency of the hemostatic agent is reduced, and if the pH is greater than 8.8, it is difficult to perform a subsequent substrate modifying step, or the structure of the substrate is broken to prevent the property from being maintained, and thus it is preferable to adjust the pH through the pretreating to have the above-described pH.

In addition, if the amount of base added in the pretreating step is less than 0.1 part by weight, the effects of scouring, degreasing, and pH control are insignificant, and if the amount of base added in the pretreating step is greater than 1 part by weight, uniform pretreatment is not possible throughout the substrate, resulting in poor quality of the substrate. Therefore, it is preferable to add the amount of base in the above-mentioned weight range.

The adsorbing the hemostatic agent is a process of causing the hemostatic agent to be adsorbed on the pretreated substrate.

The hemostatic agent adsorbed to the substrate may use at least one selected from the group consisting of thrombin, thromboplastin, fibrinogen, casein-kinase II, tissue factors, and aluminum hydroxide, and preferably, at least one or more of thrombin, fibrinogen, and aluminum hydroxide may be used.

The adsorbing the hemostatic agent is a step of applying a pretreated substrate to an aqueous solution containing a hemostatic agent and reacting the same for a predetermined time. More specifically, the substrate is immersed in purified water at 90° C. to 110° C., and a hemostatic agent is added in an amount of 2 to 5 parts by weight based on 100 parts by weight of the substrate, followed by reaction for 40 to 90 minutes. The weight ratio of the purified water and the substrate may be 4 to 6:1.

At this time, in order to increase the adsorption strength of the hemostatic agent and the base material, a fixing agent may be added together when the hemostatic agent is added, and the fixing agent may be added in an amount of 0.1 to 0.9 parts by weight based on 100 parts by weight of the base material. Sodium caseinate may be used as the fixing agent, but it is not limited thereto.

The drying is a step of drying the substrate obtained through the causing the hemostatic agent to be adsorbed, and a drying method such as natural drying, hot air drying, or cold air drying is not particularly limited.

At this time, preferably, fixing may be additionally performed between the hemostatic agent adsorbing and drying. Fixing is a step of immersing and reacting the substrate adsorbed with the hemostatic agent in the aqueous hyaluronic acid solution and is performed to prevent the hemostatic agent from falling off in the subsequent modifying step by more strongly causing the hemostatic agent to be adsorbed to the substrate.

Specifically, a substrate is immersed in a 0.1 to 0.6% aqueous solution of hyaluronic acid at a weight ratio of 1:4 to 6 and reacted at 55° C. to 80° C. for 40 minutes or more. When the concentration of the hyaluronic acid aqueous solution is not maintained within the range, the effect of preventing the falling of the hemostatic agent may be insignificant or subsequent modifying reaction efficiency may be degraded, and thus it is preferable to use the hyaluronic acid aqueous solution having the above-described concentration.

The primary modifying is a step of modifying the substrate dried through the drying step using monochloroacetic acid (MCA), and in this step, the fibers made of a cellulose material are partially carboxymethylated so that a hydrophilic carboxyl group is introduced to the surface of the fiber state substrate. Accordingly, bonding between fibers is improved, the flexibility of the fibers is increased, and as a result, physical properties of the fiber state substrate may be improved.

Specifically, the primary modifying may be performed in a multi-step manner in which the dried substrate is immersed in a solvent, a base is added, and then MCA is introduced.

The solvent may be IPA (Isopropyl Alcohol) or ethanol, and preferably IPA may be used as the solvent. When ethanol is used as the solvent, it is preferable that ethanol having a concentration of 95% or more is used. The solvent is preferably used in an amount of 50 to 70 times per 1 part by weight of the substrate. After the substrate is immersed in the solvent, it is preferable to heat the substrate to 50° C. to 70° C. and stir for 8 to 15 minutes to uniformly penetrate the solvent into the entire substrate.

Next, 2.5 to 4.5 parts by weight of a base per 1 part by weight of the substrate are added to the mixture of the solvent and the substrate while maintaining the temperature. At this time, NaOH, KOH, $Ca(OH)_2$, $Ba(OH)_2$, etc., may be used as the base, and after the base is added, the fiber surface may be modified by reacting for 75 to 120 minutes. At this time, 65% to 80% aqueous base solution may be used as the base in order to increase the miscibility.

Thereafter, a carboxyl group may be introduced to the surface of the substrate fiber by adding 3 to 5 parts by weight of MCA per 1 part by weight of the substrate at the same temperature and stirring for 120 to 180 minutes.

The secondary modifying is a step of reacting the substrate upon which the primary modifying has been completed with an organic acid aqueous solution, and through the secondary modification, the substrate reacted with the base can be appropriately neutralized, and the surface of the substrate can be stabilized.

More specifically, 50 to 70 parts by weight of the solvent are mixed with respect to 1 part by weight of the substrate on which the primary modification is completed, and after stirring at 50° C. to 70° C. for 7 to 20 minutes, 5 to 7 parts by weight of an organic acid aqueous solution is added, mixed and stirred for 30 to 50 minutes.

At this time, the organic acid aqueous solution may have a concentration of about 50% to 80%, and the organic acid may be at least one of citric acid and ascorbic acid, and preferably, both of them may be used together.

In general, when the fiber is modified using MCA, glacial acetic acid is used in the secondary modifying step, but in the case of using glacial acetic acid, there is a problem that it is difficult to use as a medical material due to irritating odors and toxicity.

Therefore, in the present disclosure, by using a mixture of citric acid and ascorbic acid that can be used for food and oral administration as an organic acid contained in an organic acid aqueous solution, the above odor and toxicity problems are solved, and biosafety is secured.

As such, when citric acid and ascorbic acid are used together as the organic acid as described above, it is preferable that the weight ratio of the citric acid and ascorbic acid is 10:2 to 5. When the weight ratio is out of the above range, that is, when the content of ascorbic acid is too low or too high, the hemostatic action of the hemostatic agent is slowed down, or the reaction of the medical material obtained through the decomposition rate control step to be described later with blood and water flow is reduced. This is because it may cause a problem that it is difficult to control the hemostasis time.

Next, washing the secondarily modified substrate is performed. The washing is a step of removing reactive substances remaining on the surface of the raw material through the preceding two modifying steps, and the substrate may be washed by immersing and stirring in the solvent used in the modifying step.

At this time, washing may be performed in multiple steps, and preferably, mixing 30 to 50 parts by weight of a solvent per 1 part by weight of the substrate and stirring for 50 to 120 minutes may be performed twice. In this case, the primary washing is preferably performed at a temperature range of 40° C. to 70° C., the secondary washing is preferably performed at room temperature, and the primary washing time longer than the secondary washing time is more preferable to improve washing efficiency.

Next, a post-treating of adjusting the pH of the washed substrate is performed to prevent side effects when applied to the body. The pH of the substrate is kept low through the previous modifying steps, and in general, the pH of the blood in the body is in the range of about 7.35 to 7.45, so the pH of the substrate should be increased to a level similar to that of the blood in the body through the post-treating.

The post-treating is a step in which 18 to 25 parts by weight of a solvent and 0.001 to 0.01 parts by weight of a base are added to 1 part by weight of the substrate and stirred at room temperature for 20 to 50 minutes. The bases used at this time are NaOH, KOH, $Ca(OH)_2$, $Ba(OH)_2$, etc., and it is preferable to use about 65% to 75% of an aqueous base solution as a base to increase the miscibility between the base and the solvent.

At this time, a decomposition rate controlling by immersing and reacting the substrate in the gelling agent diluent may be additionally performed between the washing and the post-treating.

Through this step, the surface of the substrate is coated with a gelling agent, and the gelling agent is decomposed by reacting with blood and human moisture when using medical materials. Depending on the amount of the gelling agent, the time point at which the hemostatic agent coated on the substrate is applied to the human body may be adjusted.

Specifically, decomposition rate controlling may be a step of immersing the substrate in a gelling agent diluted solution in which a gelling agent, solvent, and sodium caseinate are mixed and reacting at a temperature range of 37° C. to 45° C. for 50 to 70 minutes. At this time, when the temperature is below 37° C., it is difficult to coat the surface of the gelling agent because liquefaction of the gelling agent does not occur, and when the temperature is above 45° C., the evaporation of the solvent occurs excessively and increases the viscosity, so the decomposition rate controlling is preferably performed during the above-described reaction temperature and time.

The dilution of the gelling agent includes 5% to 20% by weight of the gelling agent, 79% to 94% by weight of the solvent, and 0.1% to 1% by weight of the fixing agent.

The gelling agent is added to control the action time of the hemostatic agent, and the action time of the hemostatic agent can be adjusted by changing the content of the gelling agent according to the use of the medical material. For example, when the content of the gelling agent is 5% by weight, the action of the hemostatic agent starts around 8 hours and can be used for trauma or surgery. When the content of the gelling agent is 10% by weight, the action of the hemostatic agent starts around 24 hours and can be used for surgery or the membrane, and when the content of the gelling agent is 15% by weight, the action of the hemostatic agent starts around 80 hours and can be used for the membrane.

As the gelling agent, at least one gelling agent selected from the group consisting of gelatin, collagen, and alginate may be used.

The solvent is used to disperse the gelling agent during the process, and IPA may be used as the solvent but is not limited thereto. The fixing agent is added to increase adhesion strength between the gelling agent and the substrate, and sodium caseinate may be used as the fixing agent but is not limited thereto.

On the other hand, the substrate that has undergone the post-treating may be dried through various drying methods such as natural drying, hot air drying, and cold air drying and then cut or molded in various shapes and sizes depending on the application, and then packaged through a sterilization step.

Hereinafter, specific actions and effects of the present disclosure will be described through an embodiment of the present disclosure. However, this is presented as a preferred example of the present disclosure, and the scope of the present disclosure is not limited according to the embodiments.

Preparation Example

First, a natural cellulose substrate made of cotton was immersed in purified water at 100° C., 0.5 parts by weight of NaOH per 100 parts by weight of the substrate was added, reacted for 50 minutes, and then the substrate was taken out, and dehydrated to complete pretreating, and pH was measured. At this time, the pH of the substrate was measured as 8.3. Next, the pretreated substrate was immersed in purified water at 100° C., and 3 parts by weight of thrombin and 0.5 parts by weight of sodium caseinate per 100 parts by weight of the substrate were added, followed by reaction for 55 minutes to adsorb the hemostatic agent to the substrate. The substrate to which the hemostatic agent was adsorbed was prepared by being immersed in a 0.3% aqueous solution of hyaluronic acid at 65° C., reacted for 50 minutes, and then naturally dried. At this time, the hyaluronic acid aqueous solution was used in an amount of 5 times the weight of the substrate.

The prepared substrate was immersed in an IPA solvent of 60 times the weight of the substrate, heated to 60° C., and stirred for 10 minutes to uniformly permeate the solvent throughout the substrate, 3.5 parts by weight of an aqueous base solution (75% NaOH) was added while maintaining the temperature and reacted for 90 minutes to modify the fiber surface. While maintaining the temperature continuously, 4 parts by weight of MCA were added per 1 part by weight of the substrate and stirred for 160 minutes to complete the primary modifying.

Next, the primarily modified substrate was immersed in an IPA solvent of 60 times the weight of the substrate, stirred at 60° C. for 15 minutes, and mixed with 6 parts by weight of an aqueous organic acid solution per 1 part by weight of the substrate, and stirred for 40 minutes to perform the secondary modifying. In this case, an organic acid aqueous solution in which citric acid and ascorbic acid were mixed in the mixing ratio (weight ratio) shown in Table 1 was used as the organic acid aqueous solution.

Thereafter, each substrate was immersed in IPA of 40 times the weight of the substrate, heated to 60° C., stirred for 90 minutes to perform primary washing, and then immersed in IPA at room temperature and stirred for 30 minutes to complete secondary washing.

The washed substrate was introduced into IPA of 20 times the weight of the substrate at room temperature, 0.005 parts by weight of a NaOH aqueous solution (70%) per 1 part by weight of the substrate was added thereto, stirred for 30 minutes, and then naturally dried.

TABLE 1

| Specimen number | Water | Citric Acid (A) | Ascorbic acid (B) | A:B (weight ratio) |
|---|---|---|---|---|
| 1 | 40 | 25 | 35 | 10:14 |
| 2 | 40 | 30 | 30 | 10:10 |
| 3 | 40 | 35 | 25 | 10:7 |
| 4 | 40 | 40 | 20 | 10:5 |
| 5 | 40 | 45 | 15 | 10:3 |
| 6 | 40 | 50 | 10 | 10:2 |
| 7 | 40 | 55 | 5 | 10:0.9 |
| 8 | 40 | 65 | — | 10:0 |

(Unit: parts by weight)

Experimental Example

First, 10 g of sodium chloride, 0.5 g of fuchsine acid, and 1 L of water were mixed to prepare a syngyna test solution used for the absorption test of tampons for menstrual treatment.

Next, 3 g of the specimen was immersed in a beaker containing 50 g of syngyna test solution and absorbed for 5 minutes, then the beaker inlet was blocked by KS-A5101 to remove syngyna test solution for 5 minutes, the weight of the specimen remaining in the beaker was measured, and the pure absorption of the specimen was calculated. At this time, three experiments were conducted for each specimen, and the results of each experiment and average values were listed in Table 2.

TABLE 2

| Specimen | Absorption amount (g) | | | |
|---|---|---|---|---|
| number | 1 time | 2 times | 3 times | Average |
| 1 | 12.8 | 12.4 | 12.7 | 12.6 |
| 2 | 13.1 | 12.4 | 12.9 | 12.8 |
| 3 | 13.4 | 13.0 | 13.2 | 13.2 |
| 4 | 14.8 | 15.2 | 15.4 | 15.1 |
| 5 | 15.1 | 14.9 | 15.8 | 15.3 |
| 6 | 15.0 | 14.7 | 14.9 | 14.9 |
| 7 | 13.4 | 13.2 | 13.5 | 13.4 |
| 8 | 12.4 | 11.5 | 12.3 | 12.1 |

According to the experimental results, the absorption amount of specimen 8 was significantly lower than that of other specimens, and from the results, it was confirmed that when citric acid and ascorbic acid were used together as the organic acid used for the secondary modifying, the absorption efficiency of the substrate was improved.

In addition, in the case of specimens 4 to 6, the absorption amount was significantly higher than that of the other specimens, which is considered to be a result of the significantly increased modifying efficiency by organic acid in the secondary modifying.

From the results of the experiments, it was confirmed that it is desirable to use citric acid and ascorbic acid together as the organic acid to increase the absorption rate of the substrate, and it was confirmed that citric acid and ascorbic acid are preferably used as the organic acid in a weight ratio of 10:2 to 5.

The present disclosure is not limited to the specific embodiments and descriptions described above, and without departing from the gist of the present disclosure claimed in the claims, anyone with ordinary skilled in the art to which the disclosure pertains can make various modifications implementation is possible, and such modifications shall fall within the protection scope of the present disclosure.

INDUSTRIAL APPLICABILITY

The present disclosure relates to a method for manufacturing a medical material capable of controlling hemostasis and decomposition rate for blood or human body water, and a medical material manufactured thereby, by causing the hemostatic component to be adsorbed on the natural cellulose substrate in the form of fibers or nonwoven fabrics, and by modifying with monochloroacetic acid (MCA) and organic acid, thereby adjusting the gelation rate. The medical material of the present disclosure has an excellent hemostatic effect, the decomposition rate of the medical material can be controlled if necessary, and the wound treating efficiency can be increased by adjusting the decomposition rate according to the purpose of using the medical material, thereby having industrial applicability.

The invention claimed is:

1. A method of manufacturing a medical material, the method comprising:

pretreating a natural cellulose substrate in the form of fiber or non-woven fabric by adjusting the pH of the natural cellulose substrate to 8 to 8.8;

causing a hemostatic agent to be adsorbed to a pretreated substrate;

drying the substrate on which a hemostatic agent is adsorbed;

primarily modifying the dried substrate using monochloro acetic acid (MCA) in the presence of a base;

secondarily modifying the primarily modified substrate to be neutralized using an organic acid aqueous solution;

washing the secondarily modified substrate by immersing and stirring the secondarily modified substrate in a solvent; and post-treating the washed substrate by adjusting the pH of the washed substrate to 7.35 to 7.45, wherein an organic acid aqueous solution used in the secondarily modifying contains citric acid and ascorbic acid in a weight ratio of 10:2 to 5.

* * * * *